(12) United States Patent
Estaba Sambrano et al.

(10) Patent No.: US 8,252,255 B2
(45) Date of Patent: Aug. 28, 2012

(54) PROCESS FOR PRODUCING PURIFIED SYNTHESIS GAS FROM SYNTHESIS GAS COMPRISING TRACE AMOUNTS OF SULPHUR CONTAMINANTS WITH A METAL-ORGANIC FRAMEWORK

(75) Inventors: Roberto Andres Estaba Sambrano, Amsterdam (NL); Renze Wijntje, Amsterdam (NL)

(73) Assignee: Shell Oil Company, Houston, TX (US)

( * ) Notice: Subject to any disclaimer, the term of this patent is extended or adjusted under 35 U.S.C. 154(b) by 24 days.

(21) Appl. No.: 12/676,475

(22) PCT Filed: Sep. 8, 2008

(86) PCT No.: PCT/EP2008/061844
§ 371 (c)(1),
(2), (4) Date: Mar. 4, 2010

(87) PCT Pub. No.: WO2009/034048
PCT Pub. Date: Mar. 19, 2009

(65) Prior Publication Data
US 2010/0207068 A1 Aug. 19, 2010

(30) Foreign Application Priority Data
Sep. 10, 2007 (EP) ..................................... 07115991

(51) Int. Cl.
*C01G 7/00* (2006.01)
*C01G 9/00* (2006.01)
*C01G 1/00* (2006.01)
*B01D 53/02* (2006.01)

(52) U.S. Cl. ............. 423/47; 423/110; 423/153; 95/135
(58) Field of Classification Search .......... None
See application file for complete search history.

(56) References Cited

U.S. PATENT DOCUMENTS

| | | | |
|---|---|---|---|
| 3,441,370 A | 4/1969 | Gutmann et al. ................. 23/2 |
| 4,359,450 A * | 11/1982 | Blytas et al. ................. 423/226 |
| 5,648,054 A * | 7/1997 | DeBerry ................. 423/226 |
| 2003/0148165 A1 | 8/2003 | Muller et al. ................. 429/34 |
| 2006/0166809 A1 * | 7/2006 | Malek et al. ................. 502/20 |
| 2007/0099038 A1 * | 5/2007 | Galloway ................. 429/17 |

FOREIGN PATENT DOCUMENTS

| | | |
|---|---|---|
| DE | 102005022844 | 11/2006 |
| DE | 102005054523 | 5/2007 |
| EP | 1674555 | 6/2006 |
| EP | 1700630 | 9/2006 |
| JP | 10099680 | 4/1998 |
| JP | 2003342260 | 12/2003 |
| WO | WO9210270 | 6/1992 |
| WO | WO9937741 | 7/1999 |
| WO | WO2004039926 | 5/2004 |
| WO | 2005049484 * | 2/2005 |
| WO | WO2006055030 | 5/2006 |
| WO | WO2006122920 | 11/2006 |
| WO | WO2007054581 | 5/2007 |
| WO | WO2007057391 | 5/2007 |
| WO | WO2008021194 | 2/2008 |

OTHER PUBLICATIONS

Dathe, H. et al. "Adsorption of SO2 on Ba Impregnated metal organic Framework Materials" Studies in Surface Science and Catalysis, 158 (2005).*
Maarten van der Burgt, et al., The Shell Middle Distillate Synthesis Process, Petroleum Review Apr. 1990 pp. 204-209.
Mueller, U., et al., "Metal-organic frameworks—prospective industrial applications," J. Mater. Chem., Journal of Materials Chemistry, 2006, vol. 16, No. 7, pp. 626-636.

* cited by examiner

*Primary Examiner* — Melvin C Mayes
*Assistant Examiner* — Sheng H Davis
(74) *Attorney, Agent, or Firm* — Charles W. Stewart

(57) ABSTRACT

The invention provides a process for producing purified synthesis gas from synthesis gas comprising sulphur contaminants in the ppmv range, the process comprising the step of: (a) contacting the synthesis gas comprising sulphur contaminants with solid sorbent comprising a metal organic framework, thereby separating sulphur contaminants from the synthesis gas to obtain purified synthesis gas.

12 Claims, No Drawings

PROCESS FOR PRODUCING PURIFIED SYNTHESIS GAS FROM SYNTHESIS GAS COMPRISING TRACE AMOUNTS OF SULPHUR CONTAMINANTS WITH A METAL-ORGANIC FRAMEWORK

The present application claims priority from European Patent Application 07115991.7 filed 10 Sep. 2007.

The invention relates to a process for producing purified synthesis gas from synthesis gas comprising trace amounts of sulphur contaminants.

Synthesis gas is rich in carbon monoxide and hydrogen and further usually contains sulphur contaminants. Producing purified synthesis gas from synthesis gas comprising trace amounts of sulphur contaminants involves removal of trace amounts of sulphur contaminants. Synthesis gas streams are generally used in catalytic chemical conversion processes. Often, desulphurization of the feedstock used for the preparation of synthesis gas is difficult to achieve or incomplete and consequently unwanted sulphur contaminants are still present in synthesis gas. Removal of these sulphur compounds to low levels is of considerable importance, because they may bind irreversibly on catalysts and cause sulphur poisoning. This results in a deactivated catalyst, which severely hampers the catalytic process. Some catalysts are even sensitive to sulphur concentrations as low as 5 to 10 ppbv. To enable the use of synthesis gas with these catalysts, sulphur contaminants need to be removed even to the ppbv range. Although bulk removal processes enable removal of sulphur contaminants to a certain level, say for example to levels in the ppmv range, for removal of trace amounts of sulphur contaminants to very low levels, in the ppbv range, different measures are needed.

Processes for removal of trace amounts of sulphur contaminants from a synthesis gas are known in the art and are generally based on solid bed adsorption processes.

For example, in U.S. Pat. No. 3,441,370 a process is described for removal of sulphur compounds from gases by passing the gases over a zinc oxide adsorbent. Removal of hydrogen sulphide is achieved at ambient temperatures. At higher temperatures, removal of RSH and COS is also possible. The zinc oxide sorbent employed has a surface area of 30 to 100 square meters per gram. The process described in U.S. Pat. No. 3,441,370 requires the presence of steam and a temperature of above 300° F. (about 149° C.). It would be desirable to have a more flexible process, enabling removal of trace amounts of sulphur at lower temperatures.

To this end, the invention provides a process for producing purified synthesis gas from synthesis gas comprising sulphur contaminants in the ppmv range, the process comprising the step of:
(a) contacting the synthesis gas comprising sulphur contaminants with solid sorbent comprising a metal organic framework, thereby separating sulphur contaminants from the synthesis gas to obtain purified synthesis gas.

Solid sorbents comprising a metal organic framework have been employed in the separation of methane from a mixture of gases including methane from other components, as described in European Patent Application EP-A-1,674,555. The gas mixtures to be purified described in EP-A-1,674,555 are relatively clean gases and do not contain any sulphur contaminants. It has now surprisingly been found that metal organic framework material can be used for removal of trace amounts of sulphur contaminants.

The process enables removal of sulphur contaminants from the ppmv range to very low levels, suitably in the ppbv range. Preferably, sulphur contaminants are removed to a level of 10 ppbv or less, more preferably 5 ppbv or less of total sulphur contaminants.

The process according to the invention can be applied to any synthesis gas, which contains sulphur contaminants in the ppmv range.

Typically, synthesis gas is generated from a feedstock such as natural gas, coal or oil residue in a synthesis generation unit such as a high temperature reformer, an autothermal reformer or a gasifier. See for example Maarten van der Burgt et al., "The Shell Middle Distillate Synthesis Process, Petroleum Review April 1990 pp. 204-209".

In those cases where the amount of sulphur contaminants in the synthesis gas leaving the synthesis gas producing unit, which can be for example a gasifier, a reformer or an autothermal reformer, exceeds 10 ppmv, the sulphur amount in the synthesis gas is preferably reduced in a bulk sulphur contaminant removal step as described hereinbefore. This results in a synthesis gas stream having an amount of sulphur contaminants of up to 10 ppmv.

The process is especially suitable for synthesis gas comprising a total amount of sulphur contaminants in the range of from 0.1 to 100 ppmv, based on the synthesis gas. In an especially preferred embodiment, the amount of sulphur contaminants, in particular $H_2S$ and COS, in the synthesis gas is up to 10 ppmv, preferably up to 5 ppmv. If the sulphur contaminants include $H_2S$, the amount of $H_2S$ is preferably up to 500 ppbv $H_2S$, still more preferably up to 300 ppbv $H_2S$ and most preferably up to 100 ppbv $H_2S$, based on the total gas.

Optionally, the process can be preceded by a bulk contaminant removal step to reduce the level of contaminants to the ppmv range. Suitable bulk contaminant removal steps include the use of one or more solvent formulations based on amines or physical solvents.

In one preferred embodiment, the bulk contaminant removal step is a process selected from the group of ADIP, Sulfinol, Flexsorb, Purisol, Rectisol and Selexol. These processes are described in Kohl and Riesenfeld, third edition. These processes are at least partly based on the finding that carbon dioxide and hydrogen sulphide are highly soluble under pressure in certain solvents, and readily releasable from solution when the pressure is reduced.

In another preferred embodiment, the bulk contaminant removal step is a process based on the direct oxidation of $H_2S$. For example, a redox process in which the $H_2S$ is directly oxidised to elemental Sulphur using an iron chelate compound while the ferric ions are reduced, followed by regeneration of the ferric ions by oxidation with air. This process is known as the SulFerox process. Another example is a combination of scrubbing the feed synthesis gas with an alkali compounds to convert $H_2S$ to $RS^-$, followed by oxidation of $RS^-$ using a biological agent. See for example WO 92/10270.

In yet another preferred embodiment, the bulk contaminant removal step is a process based on refrigirated methanol as a scrubbing solvent. When using refrigirated methanol, sulphur levels of 0.1 ppmv can be achieved. The use of refrigerated methanol is especially preferred when the synthesis gas is synthesis gas.

All the bulk contaminant removal steps mentioned hereinabove enable removal of sulphur contaminants to levels in the range of from 0.1 to 100 ppmv, or even from 0.1 to 10 ppmv.

The sulphur contaminants in the synthesis gas may include hydrogen sulpide ($H_2S$), mercaptans (RSH) and carbonyl sulphide (COS).

For purified synthesis gas, especially purified synthesis gas that is intended to be used in a catalytic chemical conversion, is often required that the concentration of sulphur contaminants is in the ppbv range, say below 10 ppbv, sometimes below 5 ppbv or even as low as at most 1 ppbv, based on the purified synthesis gas. The process according to the invention enables the production of purified synthesis gas having such a low concentration of sulphur contaminants, especially hydrogen sulphide.

In step (a), the synthesis gas comprising sulphur contaminants is contacted with a sorbent comprising a metal organic framework to separate sulphur contaminants from the synthesis gas to obtain purified synthesis gas. Separation of sulphur contaminants can take place by adsorption of sulphur contaminants from the synthesis gas onto the sorbent. Separation of sulphur contaminants may also take place by passing the sulphur contaminants to the sorbent, while purified synthesis gas stays behind onto or into the sorbent.

The temperature at which step (a) is carried out may vary between wide ranges, and is suitably between 0 and 80° C., preferably between 10 and 60° C., and more preferably at ambient temperature. Thus, the process can be carried out at relatively low temperatures. This offers considerable energy-savings compared to conventional trace removal processes where a higher temperature is needed.

The pressure at which step (a) is carried out is suitably between 1 and 150 bara, more preferably between 1 and 100 bara. Thus, the process can be carried out at high pressures. This offers advantages in the event that the synthesis gas comprising sulphur contaminants is already at a high pressure.

Preferably, the metal organic framework comprises at least one metal ion and at least one bidentate organic compound, wherein the bidentate organic compound is bound to the metal ion.

Suitably, the metal ion is an ion of a metal selected from Groups Ia, IIa, IIIa, IVa to VIIIa and Ib to VIb of the Periodic Table of the elements. References to the Periodic Table and groups thereof used herein refer to the previous IUPAC version of the Periodic Table of Elements such as that described in the 68th Edition of the Handbook of Chemistry and Physics (CRC Press). Among those metals, particular reference is made to Mg, Ca, Sr, Ba, Sc, Y, Ti, Zr, Hf, V, Nb, Ta, Cr, Mo, W, Mn, Re, Fe, Ru, Os, Co, Rh, Ir, Ni, Pd, Pt, Cu, Ag, Au, Zn, Cd, Hg, Al, Ga, In, Tl, Si, Ge, Sn, Pb, As, Sb, and Bi, more preferably to Zn, Cu, Ni, Pd, Pt, Ru, Rh and Co. Most preferred metals are Zn and Cu.

Reference herein to a bidentate organic compound is to a compound comprising at least one functional group capable to form at least two coordination bonds with the metal ion. Especially suitable bidentate organic compounds are compounds selected from the group of —COOH, —CS2H, —NO$_2$, —B(OH)$_2$, —SO$_3$H, —Si(OH)$_3$, —Ge(OH)$_3$, —Sn(OH)$_3$, —Si(SH)$_4$, —Ge(SH)$_4$, —Sn(SH)$_3$, —PO$_3$H, —AsO$_3$H, —AsO$_4$H, —P(SH)$_3$, —As(SH)$_3$, —CH(RSH)$_2$, —C(RSH)$_3$, —CH(RNH$_2$)$_2$, —C(RNH$_2$)$_3$, —CH(ROH)$_2$, —C(ROH)$_3$, —CH(RCN)$_2$ and —C(RCN)$_3$, wherein R is preferably an alkylene group with 1 to 5 carbon atoms or an arylgroup.

In an especially preferred metal organic framework the metal ion is $Cu^{2+}$ and the bidentate organic compound is benzenetricarboxylic acid. Such a metal organic framework is known as "HKUST-1" or "Cu-BTC". For the preparation of the sorbent comprising a metal organic framework, reference is made to European patent EP-A-1,674,555.

An advantage of using a sorbent comprising a metal organic framework is that the BET surface area of such a sorbent is considerably higher than the BET surface area of for example a zeolite molecular sieve. Suitably, the BET surface area of the sorbent comprising a metal organic framework is at least 500 $m^2/g$, preferably at least 1000 $m^2/g$ and more preferable at least 2000 $m^2/g$. Reference herein to the BET surface area is to the BET surface area determined using the standard method DIN 66131.

Without wishing to be bound to a particular theory of how the removal of sulphur contaminants takes place, it is believed that in most cases step (a) results in purified synthesis gas and solid sorbent comprising metal organic framework loaded with sulphur contaminants.

In general, the process will not be regenerative, as desorption of the sulphur contaminants will be difficult. It will be understood that the process is preferably carried out in a continuous mode. Thus, preferably, step (a) is performed using two or more sorbent beds, wherein at least one sorbent bed is in an adsorbing mode while at least one sorbent bed, comprising spent sorbent enriched with contaminants, is removed and replaced by a sorbent bed comprising fresh sorbent. This is usually referred to as operating using a "lead-lag" configuration. In this configuration, the synthesis gas is directed to a first bed, the so-called lead bed, which is packed with the solid adsorbent comprising a metal organic framework. The sulphur contaminants are removed from the gas by the adsorbent, and as a consequence the adsorbent will load with sulphur contaminants. When the sulphur contaminants break through the first bed they will flow into a second bed, the so-called lag bed, where fresh adsorbent comprising a metal organic framework will remove the sulphur contaminants. Once the adsorbent in the lead bed is fully loaded, the lead bed is taken offline and the adsorbent contained in it is replaced. During the time in which the lead bed is taken offline, the synthesis gas flow is directed to the lag bed.

The synthesis gas stream may be contacted with solid adsorbent either once or a plurality of times, preferably in a serial manner using more than one guard bed comprising solid adsorbent, so as to continue to reduce the content of sulphur contaminants. Using the same material in more than one cleaning or guard bed provides additional advantages. If one guard bed fails, there is immediate 'back up' to maintain guard of the catalyst material, which material is generally much more expensive than guard bed material. This back-up helps in terms of safety as well as catalyst preserver. It also allows a guard bed to be off-line for other reasons, such as reloading, regeneration, cleaning, servicing or emergencies, whilst the other(s) guard bed is maintained and the overall catalytic process continues. Using individual guard bed materials for different impurities requires the catalytic process to stop every time any guard bed material or guard bed unit must be off-line or malfunctions.

The purified synthesis gas stream comprises pre-dominantly hydrogen and carbon monoxide and very low levels, in the ppbv range, of sulphur contaminants. Preferably, the purified synthesis gas comprises levels sulphur contaminants below 0.1 ppmv, more preferably below 10 ppbv and still more preferably below 5 ppbv, based on the total purified synthesis gas. The purified synthesis gas is very suitable for conversion to chemicals in a catalytic process. Hence, the invention also comprises the purified synthesis gas. The purified synthesis gas is especially suitable for the manufacture of methanol or ethanol, the production of aldehydes using the oxo process, the production of glycols and the production of hydrocarbons.

In a preferred embodiment, the purified synthesis gas stream is contacted with a suitable hydrocarbon synthesis catalyst to form normally liquid hydrocarbons in a hydrocarbon synthesis reaction.

Preferably the purified synthesis gas stream prepared by the present invention is used in a number of chemical reactions, in particular in Fischer-Tropsch reactions or processes. Catalysts for use in the Fischer Tropsch reaction frequently comprise, as the catalytically active component, a metal from Group VIII of the Periodic Table of Elements. Particular catalytically active metals include ruthenium, iron, cobalt and nickel. Cobalt is a preferred catalytically active metal.

What is claimed is:

1. A process for producing purified synthesis gas from synthesis gas comprising a total concentration of sulphur contaminants in the range of from 0.1 to 100 ppmv, based on the synthesis gas, the process comprising the step of:
    contacting the synthesis gas with a solid sorbent comprising a metal organic framework, said metal organic framework comprising at least one metal ion bound to at least one bidentate organic compound, thereby separating sulphur contaminants from the synthesis gas to obtain purified synthesis gas containing less than 10 ppbv total sulphur contaminants.

2. A process according to claim 1, wherein step (a) is carried out at a temperature in the range of from 0 to 80° C.

3. A process according to claim 2, wherein the total concentration of sulphur contaminants in the synthesis gas from which the purified synthesis gas is produced is in the range of from 0.1 to 10 ppmv, based on the synthesis gas.

4. A process according to claim 3, wherein the purified synthesis gas comprises less than 5 ppbv of total sulphur contaminants.

5. A process according to claim 4, wherein the metal ion is an ion of Zn or Cu.

6. A process according to claim 5, wherein the metal ion is $Cu^{2+}$ and the bidentate organic compound is benzenetricarboxylic acid.

7. A process according to claim 6, wherein the metal organic framework has a BET specific surface area of at least 500 $m^2/g$.

8. A process according to claim 7, wherein the sulphur contaminants are selected from the group consisting of hydrogen sulphide, carbonyl sulphide and mercaptans.

9. A process according to claim 8, wherein the process is preceded by a bulk contaminant removal step.

10. A process according to claim 7 wherein the metal organic framework has a BET specific surface area of at least 1000 $m^2/g$.

11. A process according to claim 7, wherein the purified synthesis gas comprises less than 1 ppbv of total sulphur contaminants.

12. A process according to claim 11 wherein the metal organic framework has a BET specific surface area of at least 2000 $m^2/g$.

* * * * *